(12) United States Patent
Cane'

(10) Patent No.: US 9,220,835 B2
(45) Date of Patent: Dec. 29, 2015

(54) DEVICE FOR DRUG INFUSION

(75) Inventor: Mario Cane', Collegno (IT)

(73) Assignee: CANE' S.P.A., Rivoli (TO) (IT)

( * ) Notice: Subject to any disclaimer, the term of this patent is extended or adjusted under 35 U.S.C. 154(b) by 784 days.

(21) Appl. No.: 13/309,772

(22) Filed: Dec. 2, 2011

(65) Prior Publication Data

US 2012/0143133 A1 Jun. 7, 2012

(30) Foreign Application Priority Data

Dec. 2, 2010 (IT) ................................ TO2010A0963

(51) Int. Cl.
*A61M 5/20* (2006.01)
*A61M 5/142* (2006.01)
*A61M 5/145* (2006.01)
*A61M 5/168* (2006.01)

(52) U.S. Cl.
CPC .......... *A61M 5/1422* (2013.01); *A61M 5/14244* (2013.01); *A61M 5/14566* (2013.01); *A61M 5/16827* (2013.01); *A61M 2005/14573* (2013.01); *A61M 2206/22* (2013.01)

(58) Field of Classification Search
CPC .......... A61M 2005/1787; A61M 5/19; A61M 5/3148; A61M 5/31586; A61M 5/20; A61M 5/315; A61M 5/1422; A61M 5/14244; A61M 5/14566; A61M 5/16827; A61M 2005/14573; A61M 2206/22

USPC ..................... 604/155, 152, 173, 191, 228, 44
See application file for complete search history.

(56) References Cited

U.S. PATENT DOCUMENTS

| | | | | |
|---|---|---|---|---|
| 4,909,783 | A * | 3/1990 | Morrison | 604/30 |
| 5,957,883 | A * | 9/1999 | Lin | 604/36 |
| 7,530,976 | B2 * | 5/2009 | MacMahon et al. | 604/508 |
| 2006/0184124 | A1 * | 8/2006 | Cowan et al. | 604/155 |

* cited by examiner

Primary Examiner — Theodore Stigell
(74) Attorney, Agent, or Firm — Sughrue Mion, PLLC (57) ABSTRACT

A portable device for infusion of liquid drugs contained in a pair of syringes into a patient's body is disclosed. Said device includes a body housing a driving system and arranged to receive a pair of interchangeable syringes, and said driving system includes a single electric motor and a first and a second mechanical assembly, or a single mechanical assembly, each assembly being associated with one of the syringes or with both syringes, respectively, and being arranged to convert the rotary motion of the motor into a linear motion and to apply said linear motion to a pusher associated with the plunger of the respective syringe, both mechanical assemblies, or the single mechanical assembly, being operated for simultaneously causing the forward motion of the plunger in one syringe and the backward motion of the plunger in a second syringe.

3 Claims, 12 Drawing Sheets

DEVICE FOR DRUG INFUSION

The present invention relates to a device for drug infusion.

More precisely, the invention relates to a portable device for the infusion of liquid drugs in large amounts and/or in continuous manner.

In the medical field, drug infusion devices, more commonly referred to as "infusion pumps", are often used for administering liquid drugs through a needle introduced into the patient's body, typically into a vein or under the skin.

As therapies requiring prolonged infusion of drugs are becoming increasingly diffused, even for patients who are not confined to bed, the need has arisen to provide compact, battery-powered infusion devices, which can be easily worn by the patient.

The known devices of the above kind generally include a syringe containing the drug and removably associated with the device, and a driving unit, electronically controlled by a programmable controller, arranged to make the syringe plunger slide so as to obtain drug infusion through a cannula connected to the needle introduced into the patient's body.

Italian patents IT 1257247 and IT 1261234, Italian Utility Model IT-U-193915, European Patent EP 1078643 and European Patent Applications EP 1219312 and EP 2174679, all in the name of the Applicant, show examples of such devices.

As known, some pharmacological therapies require infusion of large amounts of drug, often substantially without interruptions. For that reason, infusion pumps capable of operating with syringes having a great capacity have been developed. Syringes having a great capacity meet the need to operate in continuous manner with large amounts of drug, but they require suitable pumping devices, the sizes of which are in contrast with the need to make the pump compact and portable.

As known, at the end of infusion, i.e. when the syringe is empty and yet the drug infusion has to be continued, it is necessary to replace the empty syringe with a full one, with a consequent more or less prolonged interruption of the infusion. In certain cases, an excessive duration of the interruption of the drug infusion can be incompatible with the favourable outcome of the pharmacological therapy the patient is subjected to. For that reason, sometimes use is made of multiple independent infusion pumps applied to a same patient in order to infuse the drug in large amounts and, if necessary, substantially without interruptions. Such a solution has however the drawback of requiring at least two pumps, with a consequent increase in the costs and the complexity of the therapy management.

In pumps for drug infusion, the starting operating conditions are restored at the end of the infusion by moving backwards the mechanically driven rod that has caused the forward movement of the syringe plunger. Since the forward movement of the rod during infusion is typically slow (actually the infusion takes place slowly due to the limit for the hourly flow rate a patient can tolerate at each infusion site), even though measures are taken in order to speed up the return of the rod to its starting position, the latter movement demands a long time, e.g. of the order of 5-10 minutes, which becomes longer as the syringe length increases. Generally therefore, even when the duration of the interruption for recharging the pump is not critical for the favourable outcome of the therapy, too long a time for restoring the operating conditions of the pump is a drawback that is appreciated neither by the patients nor by the doctors who are to operate on the pump.

It is an object of the invention to provide an infusion device, which allows solving the problem of how to reduce the time required for restoring the starting operating conditions of the pump, i.e. the conditions from which the pump can start administering the drug.

According to the invention, this object is attained by means of a device in which a pair of interchangeable and disposable syringes are coupled to a body housing a driving system of the device, and said driving system includes a single electric motor and a first and a second mechanical assembly, or a single mechanical assembly, each assembly being associated with one of the syringes or with both syringes, respectively, and being arranged to convert the rotary motion of the motor into a linear motion and to apply said linear motion to a pusher associated with the plunger of the respective syringe, both mechanical assemblies or the single mechanical assembly being operated for simultaneously causing the forward motion of the plunger in one syringe and the backward motion of the plunger in a second syringe of said pair of syringes.

Infusion pumps with a pair of syringes are known for instance from patents U.S. Pat. No. 4,065,230 and IT 1350076 and from International Patent Application WO 2009/041826. Yet, those known pumps are not portable pumps and they do dot solve the problem stated above. More particularly:

- U.S. Pat. No. 4,065,230 A and WO 2009/041826 A1 disclose pumps where both syringes are connected to a same infusion site and are so controlled that while one syringe is injecting a drug dose into the patient, the other one is being filled with a new drug dose;
- IT 1350076 A discloses a pump with two syringes intended to contain different drugs to be administered in different times and in different manners, in which the sliding of the plungers of both syringes is driven by different motors.

EP 1 634 612 discloses an apparatus for carrying out haematic infusions including a reciprocating volumetric pump comprising two cylindrical chambers having corresponding sliding pistons, said chambers being part of the pump and therefore being not interchangeable. Only the pump as a whole is replaceable. The apparatus is not portable.

In a first embodiment of the invention, and according to a first embodiment of the driving system housed in the device, both mechanical assemblies are mounted in a forward portion of the body and include each a toothed crown gear driven by a pinion integral with a shaft of the motor, an internally threaded nut, integral for rotation with said toothed crown gear, and a sliding rod, which passes through said nut, has mounted thereon the pusher at a forward end and has an external thread meshing with the thread of said nut, said rod being slidable within a respective cylindrical guide and being equipped with a radial peg slidably engaging a groove of said guide in order to prevent rotation of the rod while the latter is sliding. According to this embodiment of the invention, the internal threads of the nuts and the external threads of the sliding rods passing through the nuts are chosen so that, while a first rod is sliding in one direction, the second rod slides in the opposite direction.

In a first embodiment of the invention, and according to a second embodiment of the driving system housed in the device, both mechanical assemblies are mounted in a rearward portion of the body, and include each a toothed crown gear driven by a pinion integral with a shaft of the motor, an externally threaded stem, integral for rotation with said toothed crown gear, and an axially sliding hollow rod which has mounted thereon the pusher at a forward end and receives said threaded stem in its cavity, said rod having a smooth external surface and being provided at a rear end with an internal thread meshing with the external thread of said stem.

According to this embodiment of the invention, the internal threads of the rods meshing with the external threads of the stems are chosen so that, while a first rod is sliding in one direction, the second rod slides in the opposite direction.

In a second embodiment of the invention, the driving system includes a single mechanical assembly, which is mounted in a forward or a rearward portion of the body and includes a toothed crown gear driven by a pinion integral with a shaft of the motor, an internally threaded nut, integral for rotation with said toothed crown gear, and a sliding rod, which passes through said nut and has an external thread meshing with the thread of said nut, said rod being slidable within a respective cylindrical guide and being equipped with a radial peg slidably engaging a groove of said guide in order to prevent rotation of the rod while the latter is sliding. According to this embodiment of the invention, the rod alternately comes out from either end of the body and it is equipped with a pusher at both ends, so that, while a first pusher is sliding in one direction, the second pusher slides in the opposite direction.

Some preferred embodiments of the invention, given by way of non limiting examples, will now be described with reference to the accompanying drawings, in which.

Figure 1:
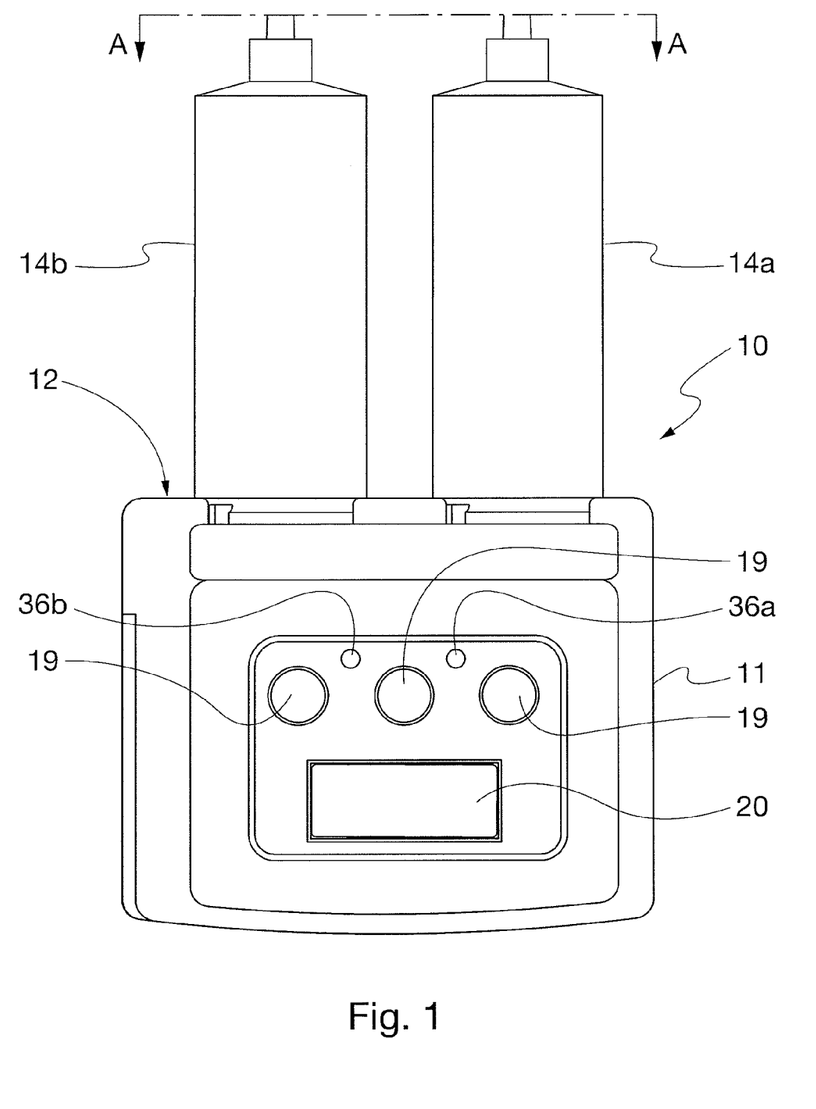
FIG. 1 is a front view of the device according to a first embodiment of the invention.
Figure 2:
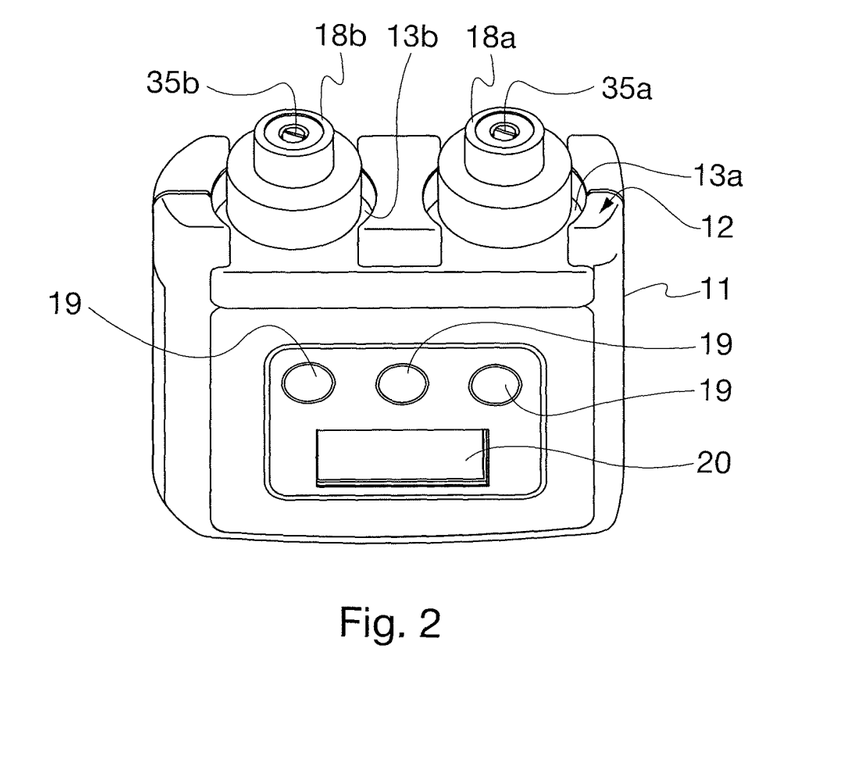
FIG. 2 is a perspective view of the casing containing the driving system of the device shown in FIG. 1.

Referring to FIGS. 1 and 2, a drug infusion pump according to the invention, generally denoted by reference numeral 10, includes a body or casing 11 with a compact size, intended to house the pump driving system, which will be disclosed below, and a pair of syringes 14a, 14b, which are preferably identical, are intended to contain for instance a same drug and are connected, through respective cannulas, not shown, to respective infusion sites in the patient's body. Syringes 14a, 14b are of an interchangeable and preferably disposable kind and are inserted side by side by means of a bayonet coupling into respective seats 13a, 13b formed in one of the bases of body 11, hereinafter referred to as front base 12. To this aim, the syringes are equipped with respective radial tabs 15a, 15b (FIG. 3A) engaging respective slots in the walls of seats 13a, 13b. Reference numerals 17a, 17b denote the syringe plungers, associated with respective pushers 18a, 18b, which are axially movable to cause the forward or backward axial sliding of the plungers, depending on the operating phase.

Body 11 is further equipped with pushbuttons 19 for controlling the different functions for which device 10 is programmed, and with a display 20 displaying e.g. the operating parameters of the device. As usual in such devices, body 11 can be associated with a strap (not shown) for the transportation of the device during use, for instance hung on the patient's neck or secured to a patient's arm.

In a starting position of the plungers (shown in the drawings and taken for instance when the device is ready for infusion), one of the pushers 18a, 18b is in a position of maximum proximity with respect to the bottom of the respective seat 13a, 13b, whereas the other pusher 18a, 18b is at the maximum distance from said respective seat 13a, 13b.

Figure 3A:
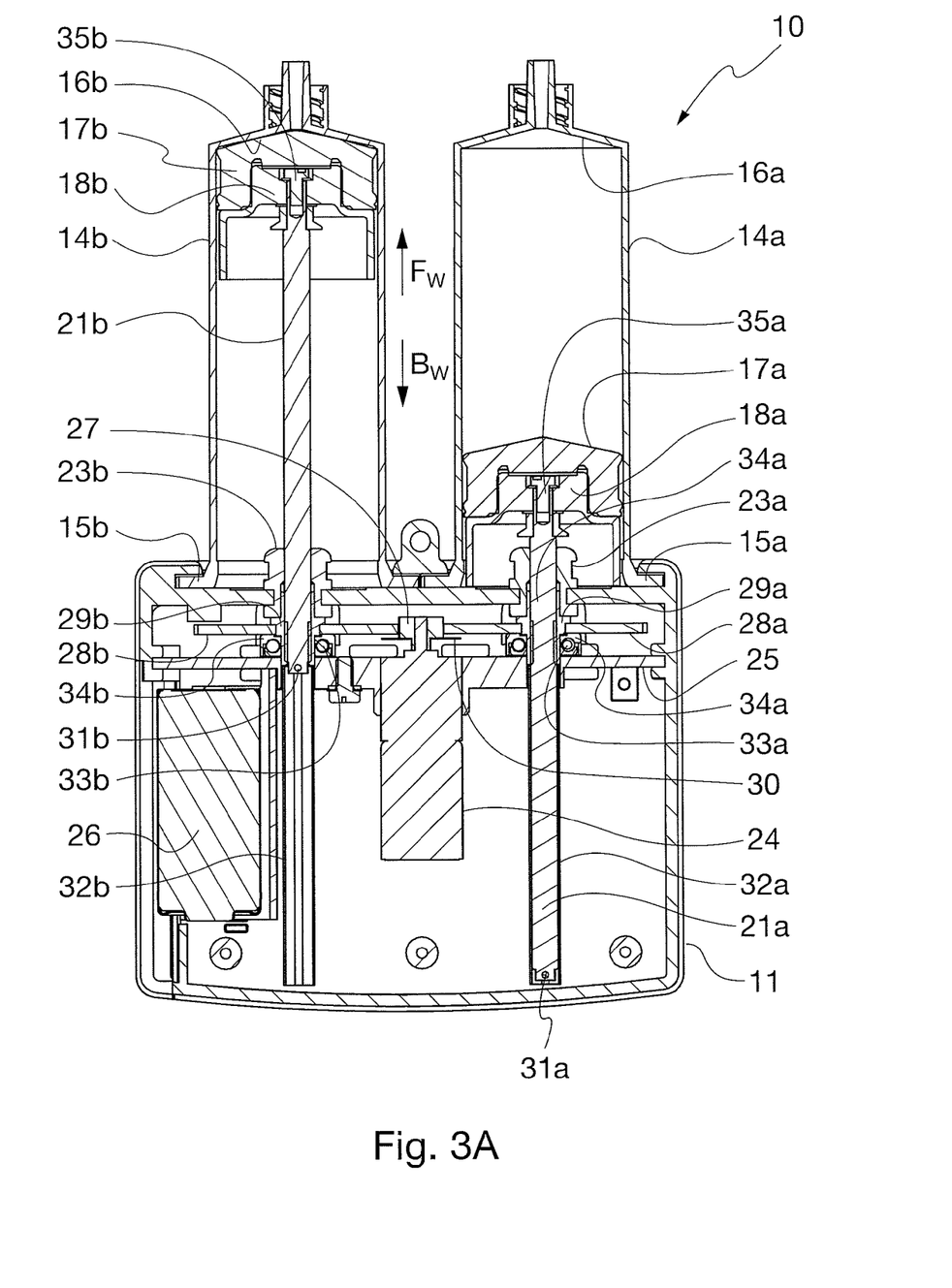
FIGS. 3A and 3B are vertical sectional views, taken according to a plane passing through line A-A in FIG. 1, showing a first embodiment of the driving system housed within the body of the device, in two different operating phases.
Figure 3B:
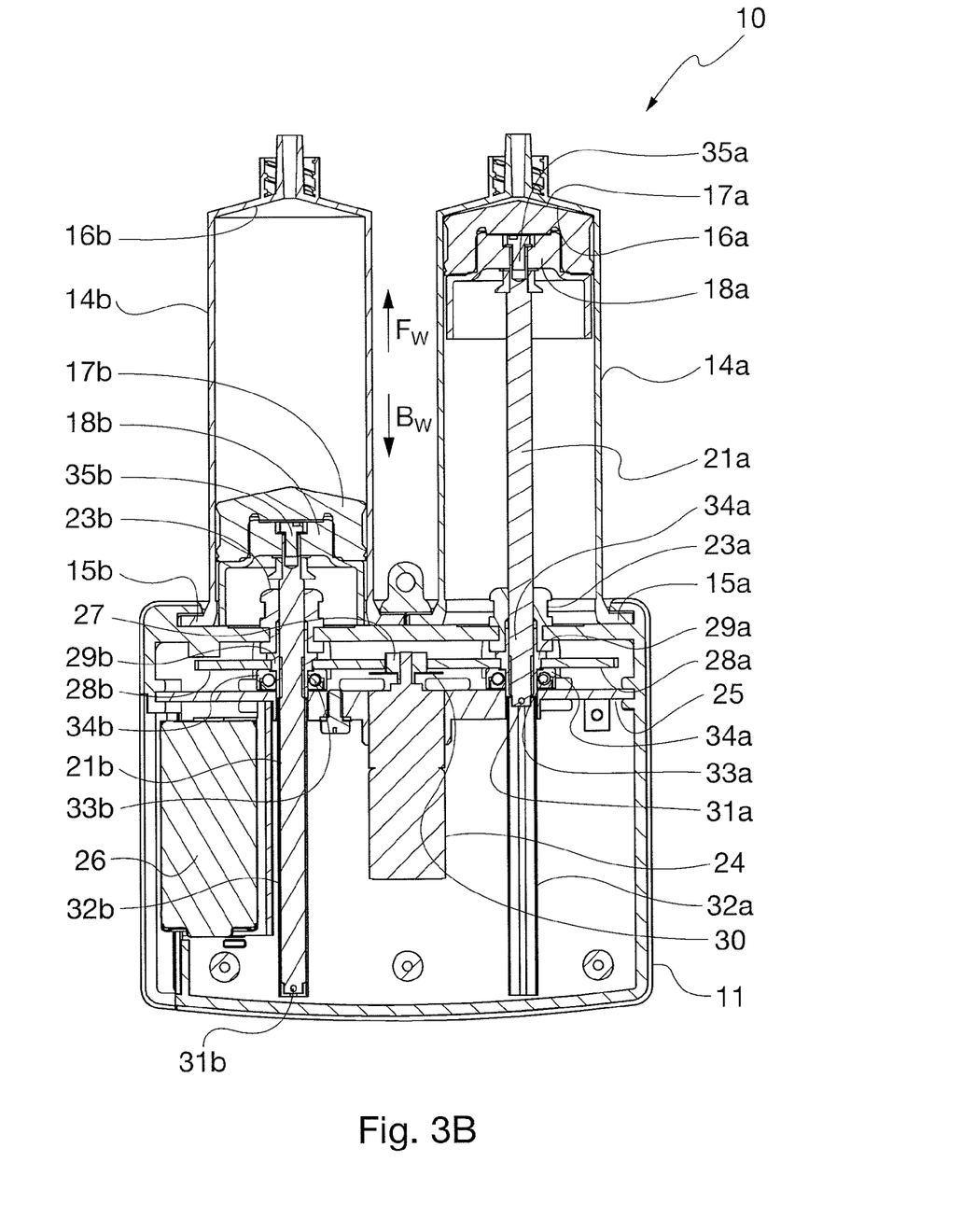

FIG. 3A shows the operating phase in which pusher 18a abuts against the bottom of seat 13a, i.e. it is in the fully retracted position, and pusher 18b abuts against plunger 17b, which in turn abuts against end 16b of syringe 14b, i.e. it is in the fully extended position. In this operating phase, the device is at the end of the infusion with syringe 14b (left syringe in the Figure) and is ready for the subsequent infusion with syringe 14a (right syringe in the Figure). FIG. 3B shows the opposite operating position, that is, when pusher 18b abuts against the bottom of seat 13b, i.e. it is in the fully retracted position, and pusher 18a abuts against plunger 17a, which in turn abuts against end 16a of syringe 14a, i.e. it is in the fully extended position. In this operating phase, the device is at the end of the infusion with syringe 14a (right syringe in the Figure) and is ready for the subsequent infusion with syringe 14b (left syringe in the Figure).

FIGS. 3A and 3B show a first embodiment of the driving system of pushers 18a, 18b, which, in this embodiment, are operated substantially in the same manner as described in EP 2174679 for a conventional infusion device with a single syringe.

The driving system includes a single electric motor 24 and a mechanical assembly for each syringe 14a, 14b, arranged to convert the rotary motion of motor 24 into a linear motion and to apply said linear motion to pusher 18a, 18b of the respective syringe. Motor 24 is borne by a supporting ferrule 25 substantially parallel to base 12 (FIGS. 1, 2) and located near said base, and is controlled by a programmable electronic controller (not shown), also housed within body 11. The provision of a single motor entails that both pushers 18a, 18b are controlled in the same manner. The motor and the controller are supplied by a battery 26.

In order to receive the linear motion, pushers 18a, 18b are secured, for instance by means of screws 35a, 35b, to the forward end of respective externally threaded, axially slidable rods 21a, 21b, which are partly received inside body 11 and come out from the latter through guiding bushings 23a, 23b mounted in corresponding openings in base 12. Between each pusher 18a, 18b and the respective guiding bushing 23a, 23b there is provided a means (not shown), for instance a bellows-like member, which surrounds the portion of the threaded rod 21a, 21b penetrating into the syringe and isolates said portion, and hence the inside of body 11, from the surrounding environment in order to prevent possible drug leaks from damaging the driving system.

The shaft of motor 24 is associated with a pinion 27 meshing with a pair of toothed crown gears 28a, 28b rigidly connected with respective internally threaded nuts 29a, 29b, whose threads engage the threads of rods 21a, 21b, respectively. Toothed crown gears 28a, 28b may have holes in order to reduce their weight, which may be relatively high, especially in applications like the one mentioned at the beginning of the description, where syringes 14a, 14b have relatively large cross-sectional areas and therefore need crown gears with quite large diameters.

Nuts 29a, 29b, by rotating about their axis, cause axial sliding of rods 21a, 21b in opposite directions thanks to the cooperation between the respective threads. Depending on the rotation direction imparted to motor 24 by the controller, the forward or backward axial sliding of rods 21*a*, 21*b*, and consequently of pushers 18*a*, 18*b*, in the direction of arrow Fw and Bw, respectively, will be obtained.

Preferably, pusher 18*a*, 18*b* rests on the body of plunger 17*a*, 17*b* without interference, so that, during the return movement of the corresponding pusher 18*a*, 18*b*, plunger 17*a*, 17*b* remains it its position against end 16*a*, 16*b* of the syringe, without generating a depression inside the syringe body. In the alternative, it is possible that the plunger and the pusher are in mutual engagement, for instance to cause drug suction during the return movement of the plunger, in order to fill the syringe.

According to the invention, the threads of rods 21*a*, 21*b* and nuts 29*a*, 29*b* associated therewith are chosen so that the rotation imparted by motor 24 causes the forward sliding of one rod 21*a*, 21*b* and the simultaneous backward sliding of the other rod 21*b*, 21*a*, that is, one thread is a right-handed thread and the other one is a left-handed thread.

By this feature, it is advantageously possible to solve the problem of how to quickly restore the starting condition of the pump at the end of an infusion. Actually, according to the invention, during drug infusion through a first syringe, it is possible to move the second pusher backwards so as to prepare it to the infusion with the second syringe.

A radial peg 31*a*, 31*b* is further provided in the rear portion of each sliding rod 21*a*, 21*b* and it is slidable inside an axial groove (not visible in the Figure) provided in a cylindrical guide 32*a* and 32*b* housing rod 21*a*, 21*b*, respectively, in order to prevent the rotation of rod 21*a*, 21*b* while allowing its axial sliding.

Toothed crown gears 28*a*, 28*b* are associated with a common position encoder 30 transmitting the signal representative of the angular position of toothed crown gears 28*a*, 28*b* and, correspondingly, of nuts 29*a*, 29*b* rigidly connected therewith, to the controller.

Sliding elements 33*a*, 33*b*, preferably consisting of ball thrust bearings or the like, are provided between supporting ferrule 25 and toothed crown gears 28*a*, 28*b*. These bearings aim at absorbing the backward thrust exerted on rods 21*a*, 21*b* due to the resistance put up by the liquid drug while leaving syringe 14*a*, 14*b* and at reducing the resulting frictions between the contacting surfaces in the mechanical members causing the forward movement of pushers 18*a*, 18*b*, which frictions could otherwise cause motor blockage. In this way, substantially only an actual occlusion along the drug flow line from one of the syringes can make the motor stop.

Pressure sensors 34*a*, 34*b*, for instance ring-like sensors, associated with rods 21*a*, 21*b*, and connected with a respective light signalling device, e.g. an LED 36*a*, 36*b* (FIG. 1) located on body 11 in the area where pushbuttons 19 and display 20 are located, will be provided between toothed crown gears 28*a*, 28*b* and thrust bearings 33*a*, 33*b* for detecting and signalling to the patient an irregular increase in the pressure applied to rods 21*a*, 21*b* because of a possible occlusion along the drug flow line from the respective syringe.

Figure 4A:
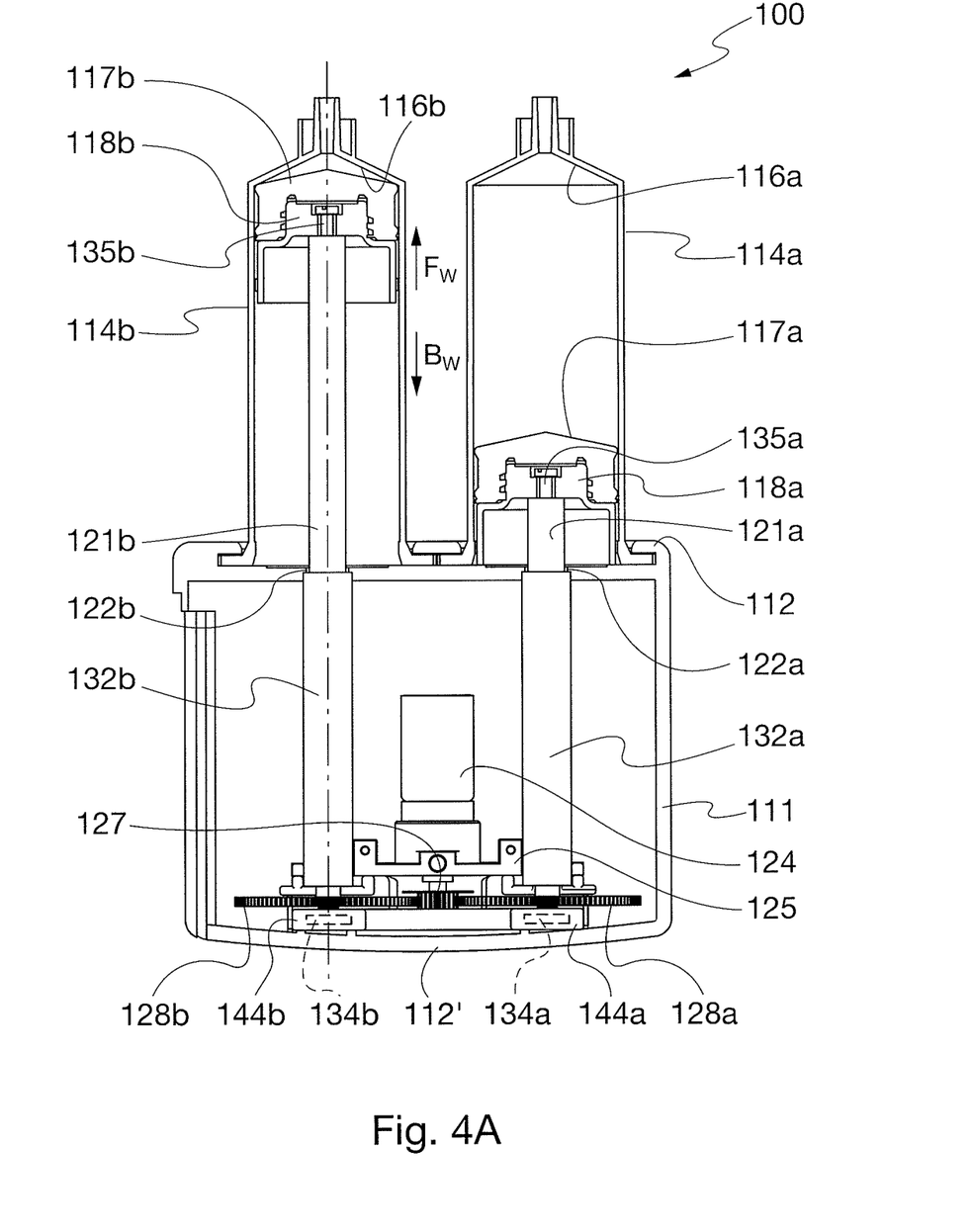
FIGS. 4A and 4B are vertical sectional views, taken according to a plane passing through line A-A in FIG. 1, showing a second embodiment of the driving system housed within the body of the device, in two different operating phases.
Figure 4B:
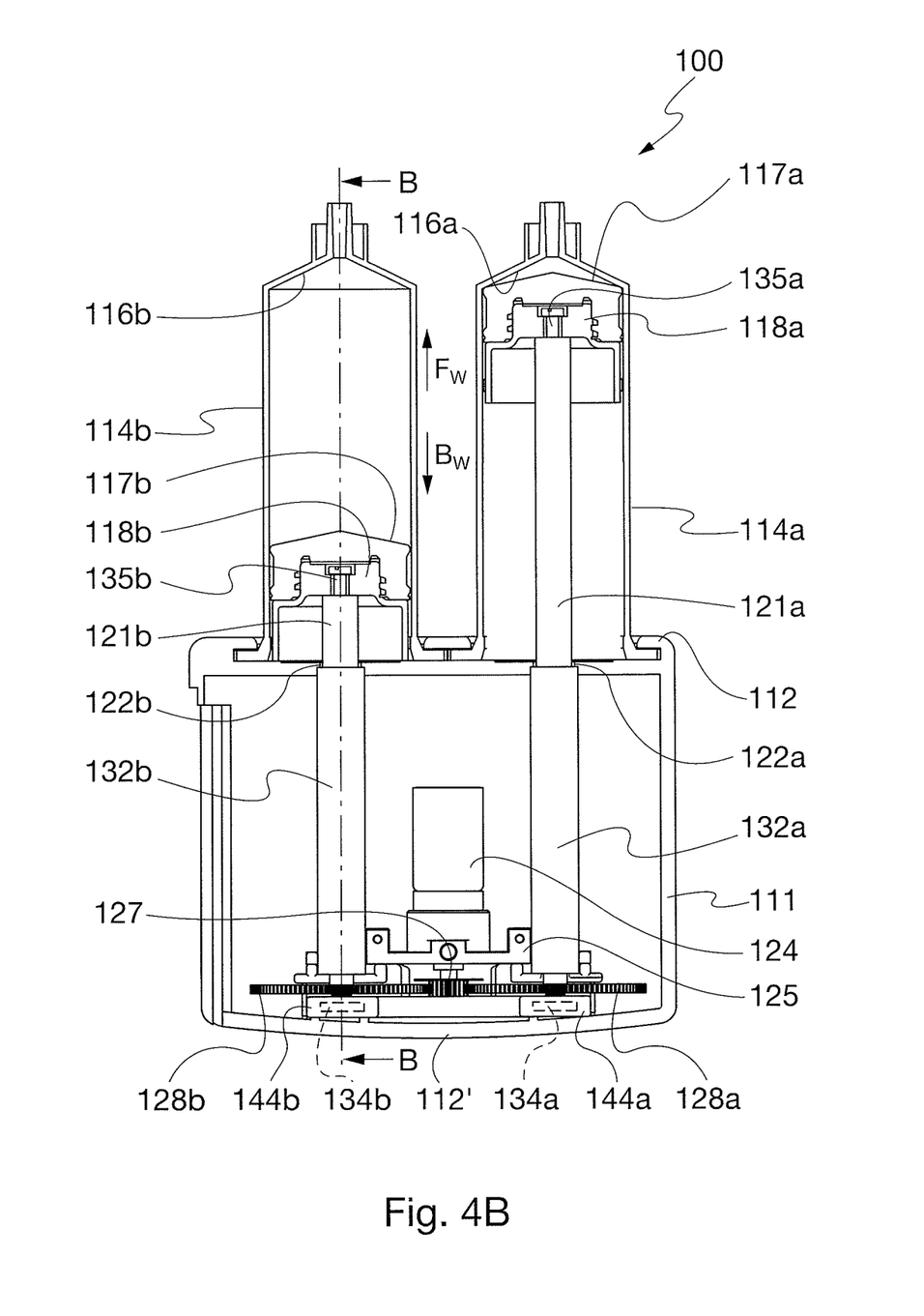
Figure 5:
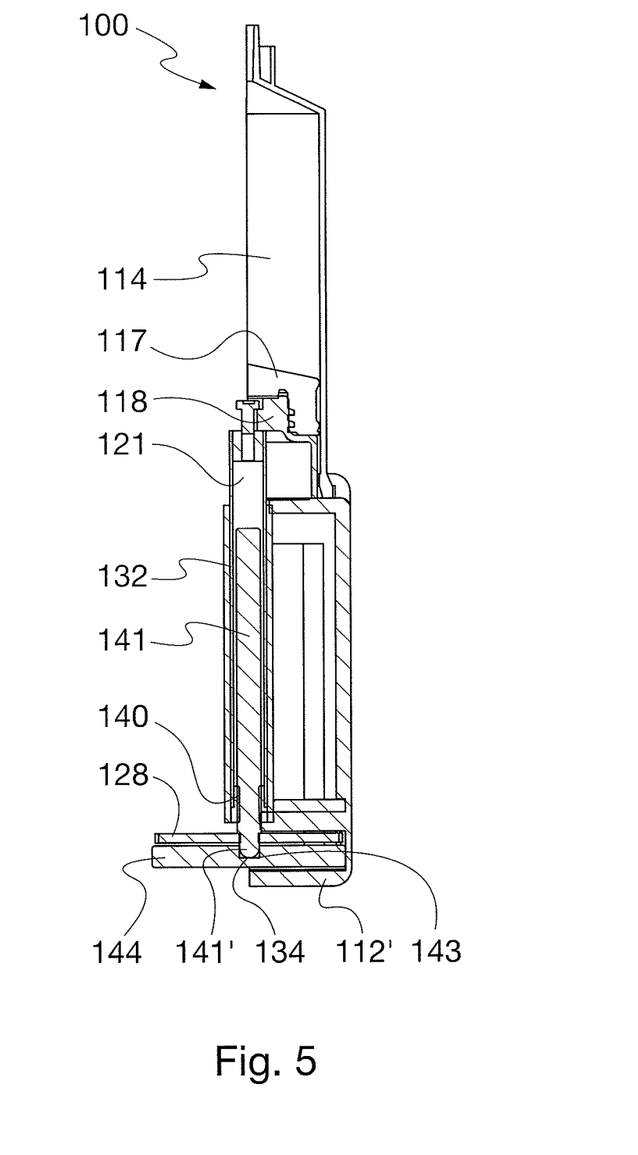
FIG. 5 is a vertical sectional view, taken according to a plane passing through line B-B in FIG. 4B.
Figure 6A:
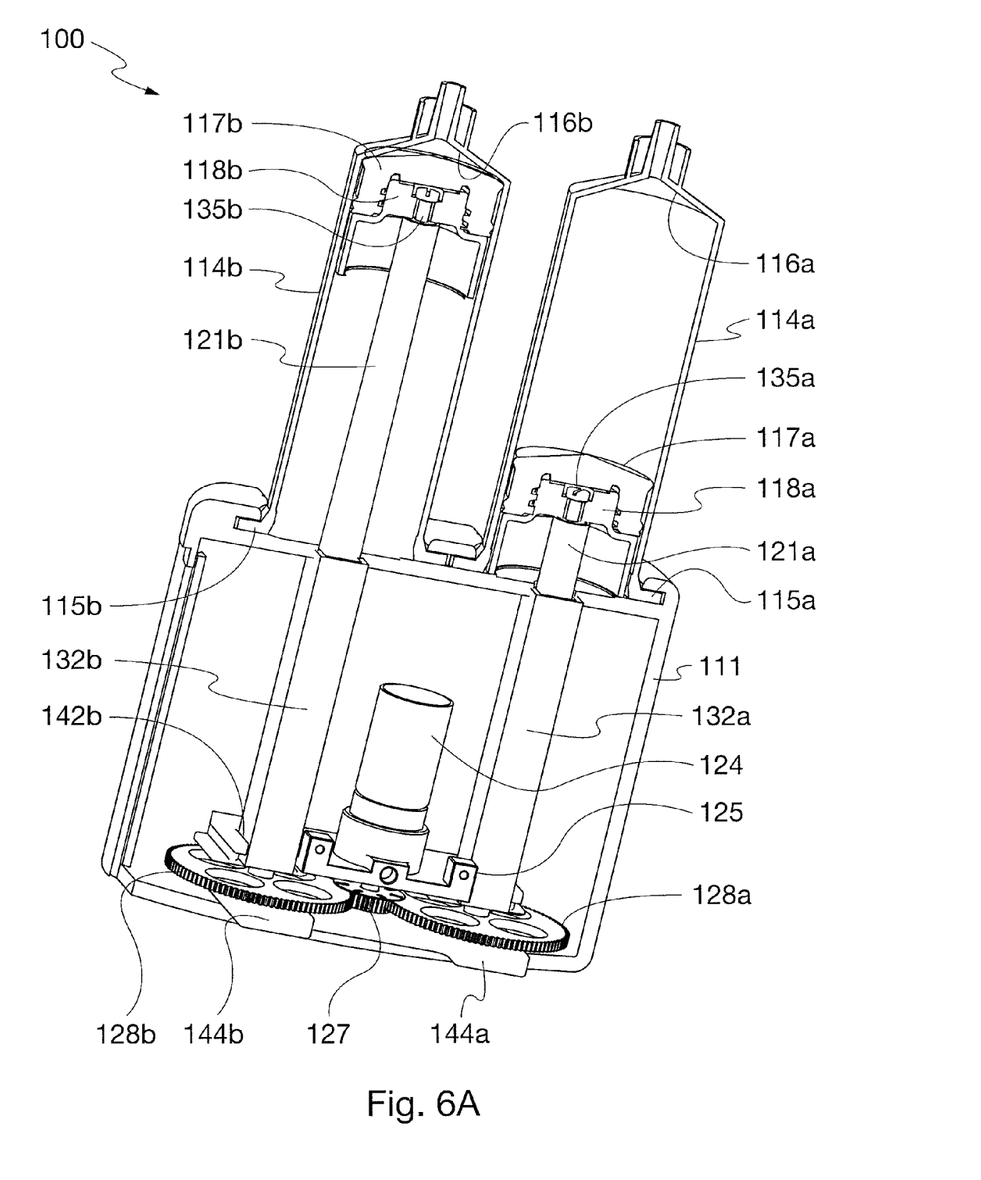
FIGS. 6A and 6B are perspective views of the sections shown in FIG. 4, in two different operating phases.
Figure 6B:
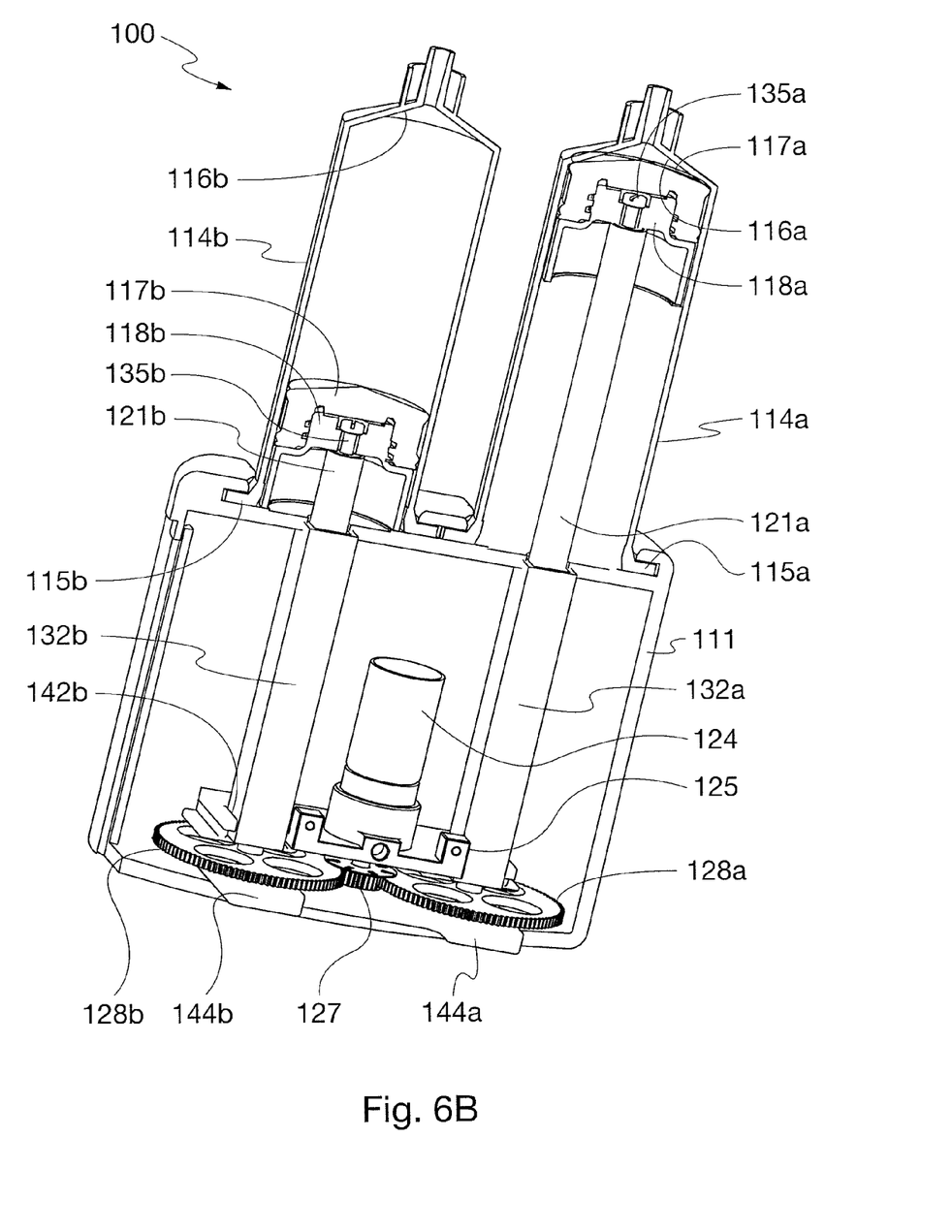

FIGS. 4 to 6 show a device 100 with a second embodiment of the driving system. In these Figures, elements corresponding to those previously described are denoted by corresponding reference numerals, preceded by digit 1. It is to be appreciated that letters a, b identifying elements associated with different syringes have been omitted in FIG. 5, where only one syringe is visible.

In this second embodiment, pushers 118*a*, 118*b* are still secured by means of screws 135*a*, 135*b* to the forward ends of respective axially slidable rods 121*a*, 121*b*, which are partly received inside body 111 and come out therefrom through openings 122*a*, 122*b* in base 112. The axial sliding of rods 121*a*, 121*b* is still driven by a common electric motor 124 through a respective mechanical assembly, arranged to convert the rotary motion of the motor 124 into a linear motion and still including pinion 127 and the pair of toothed crown gears 128*a*, 128*b*. Motor 124 and the mechanical assemblies are borne by a supporting ferrule 125 that, in this embodiment, is however located near rear base 112' of body 111.

Rods 121*a*, 121*b* are hollow cylindrical rods with smooth internal and external surfaces. An internally threaded nut 140 (FIG. 5), meshing with an externally threaded stem 141, integral for rotation with a respective toothed crown gear 128*a*, 128*b*, is secured to the rear end of each rod. Stems 141 are received in the axial cavities of rods 121*a*, 121*b*. Nuts 140 have a non-circular external cross-sectional shape, for instance a square shape, and, together with rods 121*a*, 121*b*, they slide inside guides 132*a*, 132*b*, they too for instance with square cross-sectional shape, as shown in FIGS. 6A and 6B. The rear ends of such guides are received in correspondingly shaped seats 142*a*, 142*b* formed in ferrule 125, whereas the forward ends are fastened in base 112.

Stems 141 have rounded rear ends 141' (FIG. 5) projecting from the respective crown gear 128 and abutting on the bottom of a respective recess 143 formed in supporting plates 144*a*, 144*b* borne by rear base 112' of body 111. Thanks to the rounding, the friction during rotation is reduced without need to use rolling bearings.

Each rear end 141' cooperates with a pressure sensor 134*a* and 134*b*, respectively, connected to the respective LED 36*a*, 36*b* (FIG. 1) for detecting and signalling to the patient a possible occlusion along the drug flow line from one of syringes 114*a*, 114*b*.

During operation, threaded stems 141, by rotating about their axis, cause the axial sliding in mutually opposite directions of nuts 140 and hence the simultaneous sliding in opposite directions of rods 121*a*, 121*b*, rigidly connected to nuts 140. Like in the embodiment shown in FIGS. 3A and 3B, depending on the rotation direction of motor 124, the forward or backward axial sliding of rods 121*a*, 121*b*, and consequently of pushers 118*a*, 118*b*, in the direction of arrow Fw and Bw, respectively, will be obtained.

Also in this embodiment, the pusher preferably rests on the body of the plunger without interference, so that, during the return movement of the corresponding pusher 118*a*, 118*b*, the plunger remains it its position against end 116*a*, 116*b* of the syringe, without generating a depression inside the syringe body. In the alternative, it is possible that the plunger and the pusher are in mutual engagement, for instance to cause drug suction during the return movement of the plunger, in order to fill the syringe.

The non-circular cross-sectional shape of the rods and the guides prevents the rods from rotating while sliding.

In this embodiment, the protecting bellows and the thrust bearing elements are no longer required: actually, no threaded parts penetrating into the syringe exist, and the backward thrust exerted on rods 121*a*, 121*b* due to the resistance put up by the liquid drug while going out of syringe 114*a*, 114*b* is absorbed thanks to the abutment of rear ends 141' of stems 141 against supporting plate 144. This makes the construction simpler. Moreover, dispensing with the bellows also allows having a greater available volume inside the syringes, since the space previously occupied by the members for fastening the rear ends of the same bellows is now available for increasing the plunger and piston stroke. Moreover, pressure sensors 134*a*, 134*b* may be disc-shaped sensors, which are more usual and less expensive than the ring-like sensors required by the embodiment shown in FIGS. 3A and 3B.

Figure 7A:
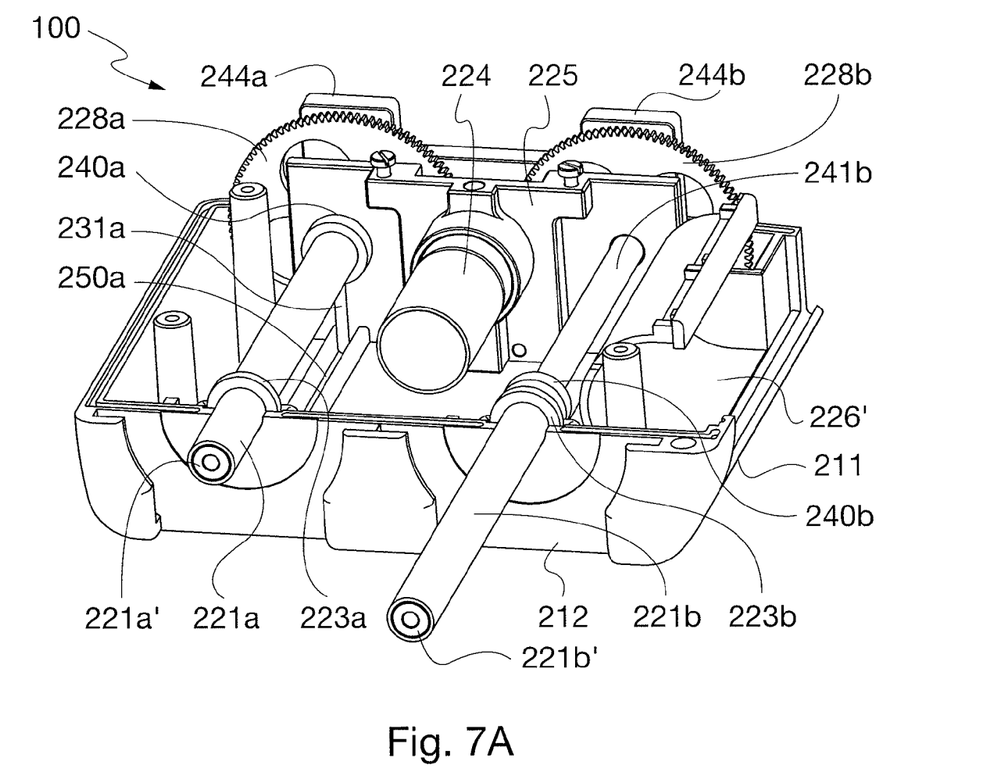
FIGS. 7A and 7B are perspective sectional views of the body of the device, showing a variant of the second embodiment of the driving system.
Figure 7B:
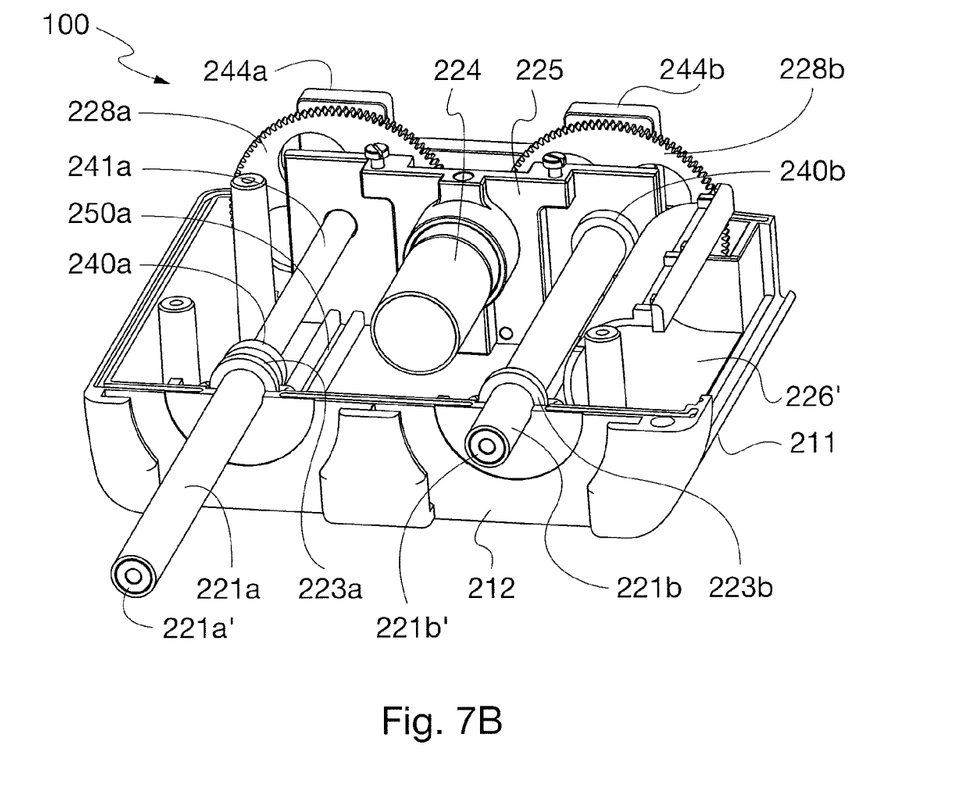

FIGS. 7A and 7B show a variant embodiment of the driving system shown in FIGS. 4 to 6. Elements corresponding to those shown in the previous Figures are denoted by corresponding reference numerals, beginning with digit 2.

In this variant embodiment, the pushers (not visible in the Figures) are still secured to respective hollow cylindrical rods 221a, 221b with smooth internal and external surfaces, and respective internally threaded nuts 240a, 240b, meshing with the externally threaded stems 241a, 241b received in axial cavities 221a', 221b' of rods 221a, 221b, are secured to the rear ends of the rods. According to the invention, the threads of the externally threaded stems and of nuts 240a, 240b are chosen so that the rotation imparted by motor 24 causes the forward sliding of one rod 221a, 221b and the simultaneous backward sliding of the other rod 221b, 221a, that is, one thread is a right-handed thread and the other one is a left-handed thread.

Nuts 240a, 240b are externally provided with radial pegs engaging guiding grooves formed in the internal surface of body 211, thereby preventing the rotation of rods 221a, 221b while they are sliding. Only peg 231a and guide 250a associated with rod 221a are visible in the Figure. By such an arrangement, nuts 240a, 240b may have any shape, for instance a cylindrical shape, and the rod guides may be simple bushings 223a, 223b located in correspondence of front base 212 of body 211. Moreover, said bushings 223a, 223b could for instance define corresponding sealing gaskets to prevent dust and liquids, for instance drug traces, from entering body 211. For that reason, bushings 223a, 223b may be made of rubber or similar material. The Figures show a seat 226' for the battery.

Figure 8A:
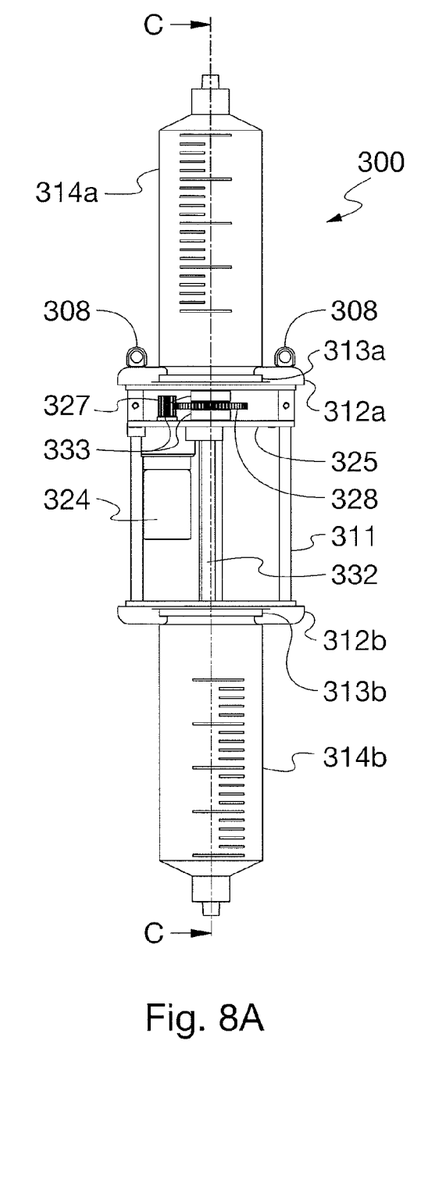
FIGS. 8A and 8B are a plan view and a sectional view taken according to a plane passing through line C-C in FIG. 8A, respectively, of a second embodiment of the invention.
Figure 8B:
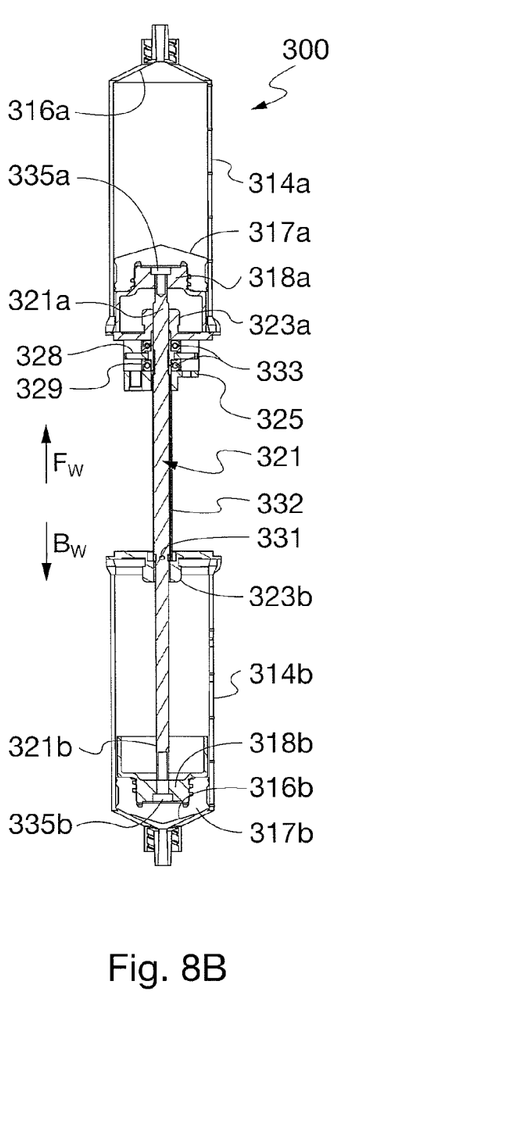

Referring to FIGS. 8A and 8B, a second embodiment of the invention is shown. Here, the drug infusion pump, generally denoted by reference numeral 300, includes a body or casing 311 with a compact size, intended to house the pump driving system, which will be disclosed below, and a pair of syringes 314a, 314b, preferably identical, which are intended to contain for instance a same drug and are connected, through respective cannulas, not shown, to respective infusion sites in the patient's body. Syringes 314a, 314b are of an interchangeable and preferably disposable kind, and are oppositely inserted, by means of a bayonet coupling, into respective seats 313a, 313b formed in the opposite bases of body 311. Said bases will be hereinafter referred to, merely by way of indication, as front base 312a and rear base 312b. To this aim, the respective radial tabs of the syringes engage respective slots in the walls of seats 313a, 313b. Reference numerals 317a, 317b denote the syringe plungers, associated with respective pushers 318a, 318b, which are axially movable forwards or backwards, depending on the operating phase.

Body 311 may be further equipped with pushbuttons for controlling the different functions for which device 300 is programmed, and with a display 320 displaying e.g. the operating parameters of the device. As usual in such devices, body 311 can be associated with a strap (not shown), for instance associated with eyelets 308 secured to one or both of bases 312a, 312b, for the transportation of the device during use, for instance hung on the patient's neck or secured to a patient's arm.

In a starting position of the plungers (shown in the drawings and taken for instance when the device is ready for infusion), one of pushers 318a, 318b is in a position of maximum proximity with respect to the bottom of the respective seat 313a, 313b, whereas the other pusher 318a, 318b is at the maximum distance from said respective seat 313a, 313b and close to end 316a, 316b of the respective syringe.

FIG. 8B shows the operating phase in which pusher 318a is close to or abuts against the bottom of seat 313a, i.e. it is in the fully retracted position, and pusher 318b abuts against plunger 317b, which in turn is close to or abuts against end 316b of syringe 314b, i.e. it is in the fully extended position. In this operating phase, the device is at the end of the infusion with syringe 314b (lower syringe in the Figure) and is ready for the subsequent infusion with syringe 314a (upper syringe in the Figure).

In this embodiment, pushers 318a, 318b are operated substantially in the same manner as described in EP 2174679 for a conventional infusion device with a single syringe.

The driving system includes a single electric motor 324 and a single mechanical assembly for both syringes 314a, 314b, which assembly is arranged to convert the rotary motion of motor 324 into a linear motion and to apply said linear motion to pusher 318a, 318b of the respective syringe. Motor 324 is borne by a supporting ferrule 325 substantially parallel to bases 312a, 312b and located near one of said bases (base 312a in the example shown), and is controlled by a programmable electronic controller (not shown), also housed within body 311. The provision of a single motor entails that both pushers 318a, 318b are controlled in the same manner. The motor and the controller are supplied by a battery also housed within body 311 of the device. Two tie-rods or small columns of said body are shown, which join the two opposite bases 312a, 312b, thereby preventing the occurrence of strains in the body made of plastics during operation of the device.

In order to receive the linear motion, pushers 318a, 318b are secured, for instance by means of screws 335a, 335b, to the opposite ends 321a, 321b of a threaded, axially slidable rod 321, which is partly received inside body 311. Said opposite ends 321a, 321b come out from body 311 through guiding bushings 323a, 323b mounted in corresponding openings in the respective opposite bases 312a, 312b.

The shaft of motor 324 is associated with a pinion 327 meshing with a toothed crown gear 328 rigidly connected with an internally threaded nut 329, whose thread engages the thread of rod 321.

Nut 329, by rotating about its axis, causes axial sliding of rod 321 and, consequently, the simultaneous backward and forward movement, respectively, of opposite ends 321a, 321b of said rods, thanks to the cooperation between the respective threads. Depending on the rotation direction imparted to motor 324 by the controller, the forward or backward axial sliding of ends 321a, 321b, and consequently of pushers 318a, 318b, in the direction of arrow Fw and Bw, respectively, will be obtained.

Also in this embodiment, the pusher preferably rests on the body of the plunger without interference, so that, during the return movement of the corresponding pusher 318a, 318b, the plunger remains it its position against end 316a, 316b of the syringe without generating a depression inside the syringe body. In the alternative, it is possible that the plunger and the pusher are in mutual engagement, for instance to cause drug suction during the return movement of the plunger, in order to fill the syringe.

According to the invention, one end 321a, 321b slides forwards and the other end simultaneously slides backwards. By this feature, it is advantageously possible to solve the problem of how to quickly restore the starting condition of the pump at the end of an infusion. Actually, according to the invention, during infusion of a drug with a first syringe, the opposite pusher is simultaneously made to move backwards so as to be prepared to the infusion with the second syringe.

Rod 321 slides inside a guide 332, for instance with square cross-sectional shape, where a longitudinal groove, not visible in the Figure, is formed. A radial peg 331 provided in the rear portion of rod 321 is slidable inside that groove in order to prevent the rotation of rod 321, while allowing its axial sliding.

Sliding elements 333, preferably consisting of ball thrust bearings or the like, are provided between supporting ferrule 325, toothed crown gear 328 and the base 312a, 312b near which toothed crown gear 328 is located. These bearings aim at absorbing the backward thrust exerted on rod 321 due to the resistance put up by the liquid drug while leaving syringe 314a, 314b and at reducing the resulting frictions between the contacting surfaces in the mechanical members causing the forward movement of pushers 318a, 318b, which frictions could otherwise cause motor blockage. In this way, substantially only an actual occlusion along the drug flow line from one of the syringes can make the motor stop.

Pressure sensors, for instance ring-like sensors connected with a respective light signalling device, e.g. a LED 36a, 36b (FIG. 31) located on body 311 in the area where the pushbuttons and the display are located, will be provided between toothed crown gear 328 and thrust bearings 333 for detecting and signalling to the patient an irregular increase in the pressure applied to the rod because of a possible occlusion along the drug flow line from the respective syringe.

It is clear that the invention allows attaining the desired objects. Thanks to the provision of two syringes controlled by a same motor, the device is compact and does not have an excessive weight, so that it is transportable by the patient without excessive trouble. A single motor keeps the costs limited and can be controlled by a controller like that employed for conventional infusion pumps with a single syringe.

It is clear that the above description has been given only by way of non-limiting example and that changes and modifications are possible without departing from the scope of the invention as defined in the following claims.

More particularly, a device capable of performing only drug infusion has been described and shown: it is however self-evident that the driving system may include the features disclosed in EP 2174679, so as to enable also drug suction into the syringes.

Moreover, in the driving systems shown herein, the pinion directly meshes with the toothed crown gears. However, it is self-evident that one or more reduction stages can be arranged between the pinion and the toothed crown gears: this allows using crown gears with smaller diameters and, by a proper choice of the gears, reducing the overall weight of the same gears.

Further, in the embodiments where the pushers are secured to smooth rods, it is possible to form the thread intended to engage the threaded stems directly on the internal surface of the corresponding rod. In such case, in the embodiment shown in FIGS. 4 to 6, the end portions of the rods must obviously have non circular external cross-sections.

The invention claimed is:

1. A portable device for infusion of liquid drugs contained in at least one syringe into a patient's body, said device including a body housing a driving system, wherein a pair of interchangeable syringes, each arranged to be connected to the same infusion site or to different infusion sites, are receivable by said body, and said driving system includes a single electric motor and a first and a second mechanical assembly, each assembly being associated with one of the pair of syringes, and being arranged to convert the rotary motion of the motor into a linear motion and to apply said linear motion to a pusher associated with a plunger of the respective syringe of the pair of syringes, both mechanical assemblies being operated for causing simultaneous forward motion of the plunger in one of the pair of syringes and backward motion of the plunger in the other of the pair of syringes; and wherein said motor and said first and second mechanical assemblies are mounted in a forward portion of the body, and wherein each of said first and second mechanical assemblies includes: a toothed crown gear driven by a pinion integral with a shaft of the motor; an internally threaded nut, integral for rotation with said toothed crown gear; and a sliding rod, which passes through said nut, has mounted thereon the pusher at a front end and has an external thread meshing with the thread of said nut, and in that said rod is slidable within a respective cylindrical guide and is equipped with a peg slidable in a groove of said guide in order to prevent rotation of the rod while the latter is sliding.

2. The device as claimed in claim 1, wherein at least one sliding element is arranged between the toothed crown gear of each mechanical assembly and a ferrule supporting the motor, which element is arranged to absorb the backward thrust applied onto the rod by the resistance put up by the liquid drug in leaving the respective syringe of the pair of syringes and to reduce the resulting friction between contacting surfaces in said first and second mechanical assemblies.

3. The device as claimed in claim 1, wherein at least one sliding element is arranged between the toothed crown gear of each mechanical assembly and a ferrule supporting the motor, which element is arranged to absorb the backward thrust applied onto the rod by the resistance put up by the liquid drug in leaving the respective syringe of the pair of syringes and to reduce the resulting friction between contacting surfaces in said first and second mechanical assemblies, so that substantially only an actual occlusion along a drug flow line from said syringe can make the motor stop.

* * * * *